United States Patent [19]

Schmolka

[11] Patent Number: 4,511,563
[45] Date of Patent: Apr. 16, 1985

[54] CLEAR ANALGESIC GELS WITH REDUCED TACKINESS

[75] Inventor: Irving R. Schmolka, Grosse Ile, Mich.

[73] Assignee: BASF Wyandotte Corporation, Wyandotte, Mich.

[21] Appl. No.: 514,293

[22] Filed: Jul. 15, 1983

[51] Int. Cl.$^3$ .................... A61K 9/10; A61K 31/60; A61K 47/00
[52] U.S. Cl. .................... 514/162; 424/78; 514/164; 514/772; 514/788
[58] Field of Search .................... 424/78, 230, 358

[56] References Cited

U.S. PATENT DOCUMENTS

| | | | |
|---|---|---|---|
| 2,422,145 | 6/1947 | Taylor | 426/651 |
| 2,435,744 | 2/1948 | Hartman | 426/651 |
| 2,508,978 | 5/1950 | Tribble | 426/651 |
| 2,677,700 | 5/1954 | Jackson | 424/49 |
| 2,773,801 | 12/1956 | Fox | 424/49 |
| 2,828,345 | 3/1958 | Spriggs | 260/615 |
| 3,639,563 | 2/1972 | Januszewsky | 424/49 |
| 3,666,496 | 5/1972 | Honey et al. | 426/651 |
| 3,674,502 | 7/1972 | Honey et al. | 426/651 |
| 3,947,570 | 3/1976 | Pensak et al. | 424/49 |
| 4,130,638 | 12/1978 | Dhabhar et al. | 424/49 |
| 4,150,151 | 4/1979 | Pader et al. | 424/49 |

FOREIGN PATENT DOCUMENTS 7709273  2/1979  Netherlands .................... 424/365

OTHER PUBLICATIONS

BASF Wyandotte, C.A. 78, #33936y, (1973), of Brit. 1,292,640, 11 Oct. 1972.
Collette et al., C.A. 84, #111574u, (1976), of J. Pharm. Pharmacol., 1975, 27(9P): 27.
Shen et al., C.A. 86, #34210j, (1977), of J. Pharm. Sci., 1976, 65(12): 1780-3.
Cantor et al., C.A. 93, #54000p, (1980), of Can. 1,072,413, 26 Feb. 1980.
Collett et al., C.A. 92, #135284r, (1980), of J. Pharm. Pharmacol., 1979, 31, 80P.
Chen-Chow, C.A. 92, #220628a, (1980), of Diss. Abstr. Int. B., (1980), 40(1D7: 4751-2.
Chen-Chow et al., C.A. 95, #175711w, (1981), of Acta Pharm. Suec., 1981, 18(4): 239-244.
Nippon Oils & Fats, C.A. 97, #203233d, (1982), of Jpn. Kokai Tokkyo Koho, JP82 128636, 10 Aug. 1982.

Primary Examiner—Shep K. Rose
Attorney, Agent, or Firm—William G. Conger; David L. Hedden; Joseph D. Michaels

[57] ABSTRACT

The subject invention relates to analgesic gels which comprise
1. from 5 to 15 parts of an analgesic compound;
2. from 10 to 40 parts of a nonionic surfactant which forms a gel in water alone at about 15 to 30 percent by weight based upon the weight of the water plus the weight of the nonionic surfactant;
3. from 5 to 40 parts of glycerin;
4. from 40 to 75 parts of water; and
5. optional ingredients (q.v.)

said parts based upon 100 parts of the composition and provided that the weight ratio of nonionic surfactant to water is from 5:1 to 3:1.

The subject gels are clear, water soluble and are not tacky when applied to the skin.

8 Claims, No Drawings

CLEAR ANALGESIC GELS WITH REDUCED TACKINESS

BACKGROUND OF THE INVENTION

1. Field of the Invention

The subject invention relates to clear analgesic gels. The gels comprise an analgesic compound, certain nonionic surfactants, glycerin, water, and optional ingredients.

2. Description of the Prior Art

Analgesic compositions are well known in the art. However, these compositions are creams or lotions and are not clear. Consequently, they do not have the aesthetically desirable appearance of a clear product. It would be desirable to have clear products, particularly if they were not tacky when applied to the skin.

SUMMARY OF THE INVENTION

The subject invention relates to analgesic gels which comprise 1. from 5 to 15 parts of an analgesic compound;
2. from 10 to 40 parts of a nonionic surfactant which forms a gel in water alone at about 15 to 30 percent by weight based upon the weight of the water plus the weight of the nonionic surfactant;
3. from 5 to 40 parts of glycerin;
4. from 40 to 75 parts of water; and
5. optional ingredients (q.v.), said parts based upon 100 parts of the composition and provided that the weight ratio of nonionic surfactant to water is from 1:2 to 1:5.

The subject gels are clear, water soluble and are not tacky when applied to the skin.

DESCRIPTION OF THE PREFERRED EMBODIMENT

For purposes of this invention, an analgesic compound will be defined as a compound which is capable of relieving pain by altering the perception of pain producing stimuli without producing anesthesia whether it be local or general. Illustrative examples of such compounds are triethanolamine salicylate, camphor, camphor combined with phenol, benzyl alcohol, camphorated metacresol, sodium phenolate, menthol, and resorcinol. In cases where the analgesic compound is insoluble in the aqueous gel, an organic solvent, such as an alcohol, may be added to dissolve the analgesic compound.

As was mentioned, the nonionic surfactants used are those which form gels in water alone at about 15 to 30 percent by weight. Of particular interest as nonionic surfactants are compounds selected from the group consisting of polyoxybutylene-polyoxyethylene copolymers, polyoxyethylene-polyoxypropylene copolymers, polyoxyethylated polypropylene glycol adducts of ethylenediamine, and mixtures thereof. These particular nonionic surfactants are well known in the art.

The polyoxybutylene-polyoxyethylene copolymers which can be used are a cogeneric mixture of conjugated polyoxybutylene-polyoxyethylene compounds having as a hydrophobe, a polyoxybutylene polymer of at least 1200 molecular weight. The polyoxybutylene compounds are prepared by first condensing butylene oxide with an organic compound containing a plurality of reactive hydrogen atoms to prepare a polyoxybutylene polymer of at least 1200 molecular weight, and subsequently condensing ethylene oxide thereto. Methods for preparing these compounds are described in U.S. Pat. No. 2,828,345 and British Pat. No. 722,746 which are hereby incorporated by reference. The compounds used in this invention conform to the following generic formula:

$$Y[(C_4H_8O)_n\text{—E—H}]_x \qquad \text{(I)}$$

wherein Y is the residue of a water soluble organic compound containing therein x active hydrogen atoms; n is an integer; x is an integer greater than 1; the values of n and x are such that the molecular weight of the compound, exclusive of E, is at least 1200, as determined by hydroxyl number; E is a polyoxyalkylene chain wherein the oxygen/carbon atom ratio is at least 0.5, and E constitutes 45 percent by weight to 85 percent by weight of the compound.

The compounds are characterized in that all the hydrophobic oxybutylene groups are present in chains bonded to the organic radical at the site of a reactive hydrogen atom thereby principally constituting a polyoxybutylene polymer. The hydrophilic oxyethylene groups are bonded to the polyoxybutylene polymer in polyoxyethylene chains. The average molecular weight of the hydrophobic groups is at least 1200, as determined by hydroxyl number, and the hydrophilic oxyethylene groups present constitute 45 to 85 percent by weight of the compound with the provisos that (a) when the polyoxybutylene hydrophobe molecular weight is about 1200, then the minimum polyoxyethylene content is about 60 percent by weight of the block copolymer and the minimum block copolymer content to form a gel is about 25 percent by weight of the gel composition;

(b) when the polyoxybutylene hydrophobe molecular weight is about 1800, then the minimum polyoxyethylene content is about 55 percent by weight of the block copolymer and the minimum block copolymer content to form a gel is about 20 percent by weight of the gel composition;

(c) when the polyoxybutylene hydrophobe molecular weight is about 2400, then the minimum polyoxyethylene content is about 50 percent by weight of the block copolymer and the minimum block copolymer content to form a gel is about 16 percent by weight of the gel composition;

(d) when the polyoxybutylene hydrophobe molecular weight is about 3000, then the minimum polyoxyethylene content is about 45 percent by weight of the block copolymer and the minimum block copolymer content to form a gel is about 16 percent by weight of the gel composition.

The polyoxyethylene-polyoxypropylene block copolymers which can be used as the nonionic surfactant can be represented by the following formula:

$$\text{HO}(C_2H_4O)_b(C_3H_6O)_a(C_2H_4O)_b\text{H} \qquad \text{(II)}$$

wherein a is an integer such that the hydrophobe base represented by $(C_3H_6O)$ has a molecular weight of at least 2250, the gel contains at least 40 percent by weight of the block polymer and b in formula (II) is at least 26. When the hydrophobe has a molecular weight of 4000, the gel contains at least 20 percent by weight of the block polymer and b in formula (II) is at least 136.

Not all of the block polymers of formula (II) can be used. Additional information regarding which compounds can be used can be obtained from U.S. Pat. No. 3,740,421, which is hereby incorporated by reference.

The polyoxyethylated polyoxypropylene glycol adducts of ethylene diamine which can be used as the nonionic surfactant may be represented by the following formula:

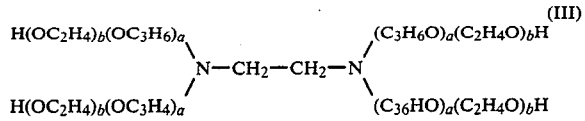
(III)

wherein a and b are integers such that the polymers may have (1) a hydrophobe molecular weight of from about 2000 to about 8000, (2) a hydrophile content of from 10 percent to 90 percent by weight, and (3) a total molecular weight of from about 4000 to 100,000.

The hydrophobe base of the polymers of formula III above is prepared by adding propylene oxide to the four hydroxyl groups of ethylene diamine. To be useful in the present invention, the hydrophobe base must have a molecular weight of at least about 2000, preferably from 4500 to 7000. By adding ethylene oxide to the hydrophobe base, it is possible to put polyoxyethylene hydrophile groups on the ends of the molecule. These hydrophile polyoxyethylene groups may be controlled to constitute anywhere from 10 percent to 90 percent by weight of the polymer.

Not all of the block copolymers of formula III can be used. Additional information regarding which copolymers can be used can be obtained from U.S. Pat. No. 3,579,405, which is hereby incorporated by reference.

As was mentioned, glycerin is also one of the essential ingredients in the subject composition. Glycerin is used in the compositions to reduce their tackiness. Glycerin is effective at achieving this, but will not interfere with the gel characteristics. This result is surprising because comparative data show that if propylene glycol or trimethyolpropane is used instead of glycerin, a gel will not form. Moreover, additional glycerin can be used to strengthen the gel. Furthermore, since the use of glycerin enables the formulator to use less nonionic surfactant, the cost of the gel is reduced.

Other optional ingredients may be incorporated into the analgesic gel provided that they are innocuous to the stratum corneum. They include such products as glycols, lanolin, lanolin derivatives, perfumes, preservatives, fatty esters, emollients, natural oils, fatty acids, fatty alcohols and derivatives, pigments, or dyes, etc. Other surface active agents, especially anionic or cationic, as well as non-block polymer nonionic surfactants, should be kept to a minimum (10 percent by weight or less of the total product) or they may weaken or destroy the gel characteristics.

The procedure used to prepare these gels is well known and either the hot or cold technique may be utilized. The cold technique involves dissolving the ingredients at a temperature of about 5° to about 10° C. When solution is complete, the system is brought to room temperature whereupon it forms a gel. If the hot technique is employed, the water is placed in a container, the other ingredients are added and the mixture is heated to 75° C. to 85° C. with slow stirring until a clear homogeneous solution is obtained. Upon cooling to room temperature, a clear gel is formed.

As used herein, the term "gel" is defined as a solid or semisolid colloid containing quantities of water. The colloidal solution with water as a dispersion medium is often called a "hydrosol." The gels within the scope of the present invention are more specifically "ringing" gels and may be described as gels that have a firm, jelly-like consistency; that is, by tapping the gel lightly, it will vibrate and return to its original configuration.

The following Examples will illustrate specifically how to prepare analgesic gels within the scope of this invention. They are not intended, however, to limit it in any way. The parts referred to in the Examples are by weight.

EXAMPLES

The following analgesic gels were prepared by the hot technique described previously. The Table which follows shows the amounts of the various ingredients used. The surfactants used in the Examples are described as follows:

Surfactant A—a propylene glycol initiated polyoxypropylene-polyoxyethylene nonionic surfactant having an average polyoxypropylene hydrophobe of 4,000 molecular weight and a polyoxyethylene hydrophile content of about 70 percent by weight of the surfactant.

Surfactant B—a propylene glycol initiated polyoxypropylene-polyoxyethylene nonionic surfactant having an average polyoxypropylene hydrophobe of 3,250 molecular weight and a polyoxyethylene hydrophile content of about 70 percent by weight of the surfactant.

Surfactant C—an N,N,N',N'-tetrakis(2-hydroxylpropyl)ethylenediamine initiated polyoxypropylene-polyoxyethylene nonionic surfactant having an average polyoxypropylene hydrophobe of 6,500 to 7,000 molecular weight and a polyoxyethylene hydrophile content of about 80 percent by weight of the surfactant.

Surfactant D—a 1,4-butanediol initiated polyoxybutylene-polyoxyethylene nonionic surfactant having an average polyoxybutylene hydrophobe of 3,000 molecular weight and a polyoxyethylene hydrophile content of about 80 percent by weight of the surfactant.

TABLE

|  | 1 | 2 | 3 | 4 | 5 | 6 | 7 | 8 | Comparison Examples | | |
|---|---|---|---|---|---|---|---|---|---|---|---|
|  |  |  |  |  |  |  |  |  | 9 | 10 | 11 |
| Water | 66.9 | 63.3 | 60.8 | 52.8 | 47.8 | 47.4 | 59.3 | 59.8 | 47.8 | 47.9 | 69.0 |
| QUADROL ® polyol | 5.4 | — | 8.2 | 8.2 | — | — | — | 8.2 | 9.4 | 8.2 | 5.4 |
| Triethanolamine | — | 5.4 | — | — | 8.2 | 4.1 | 5.4 | — | — | — | — |
| Salicylic Acid | 2.7 | 5.3 | 4.0 | 4.0 | 4.0 | 3.5 | 5.3 | 4.0 | 2.8 | 3.9 | 2.6 |
| Glycerin | 5.0 | 5.0 | 5.0 | 15.0 | 25.0 | 30.0 | 5.0 | 10.0 | — | — | — |
| Propylene Glycol | — | — | — | — | — | — | — | — | 25.0 | — | — |
| Trimethylolpropane | — | — | — | — | — | — | — | — | — | 25.0 | — |
| Surfactant A | 20.0 | 21.0 | 22.0 | 20.0 | 15.0 | 15.0 | — | — | 15.0 | 15.0 | 15.0 |
| Surfactant B | — | — | — | — | — | — | 25.0 | — | — | — | — |
| Surfactant C | — | — | — | — | — | — | — | — | — | — | — |
| Surfactant D | — | — | — | — | — | — | — | 18.0 | — | — | — |

TABLE-continued

| | | | | | | | | Comparison Examples | | |
|---|---|---|---|---|---|---|---|---|---|---|
| 1 | 2 | 3 | 4 | 5 | 6 | 7 | 8 | 9 | 10 | 11 |
| 100.0 | 100.0 | 100.0 | 100.0 | 100.0 | 100.0 | 100.0 | 100.0 | 100.0 | 100.0 | 100.0 |

All of the formulations in Examples 1–8 resulted in sparkling clear gels at 20° C. which were not tacky when applied to the skin. On the other hand, a gel was not formed when formulations corresponding to Comparative Examples 9–10 were mixed. Although the formulation for Comparative Example 11 did result in a gel, the gel was tacky when applied to the skin.

The embodiments of the invention in which an exclusive privilege or property is claimed are defined as follows:

1. An analgesic gel which comprises
   (a) from 5 to 15 parts of an analgesic compound;
   (b) from 10 to 40 parts of a nonionic surfactant which forms a gel in water alone at about 15 to 30 percent by weight based upon the weight of the water plus the weight of the nonionic surfactant;
   (c) from 5 to 40 parts of glycerin;
   (d) from 40 to 75 parts of water; and
   (e) optional ingredients (q.v.), said parts based upon 100 parts of the composition and provided that the weight ratio of nonionic surfactant to water is from 1:2 to 1:5.

2. The gel of claim 1 wherein the analgesic compound is triethanolamine salicylate.

3. The gel of claim 1 wherein the nonionic surfactant is selected from the group consisting of polyoxybutylene-polyoxyethylene copolymers, polyoxyethylene-polyoxypropylene copolymers, polyoxyethylated polypropylene glycol adducts of ethylenediamine, and mixtures thereof.

4. The gel of claim 2 wherein the nonionic surfactant is selected from the group consisting of polyoxybutylene-polyoxyethylene copolymers, polyoxyethylene-polyoxypropylene copolymers, polyoxyethylated polypropylene glycol adducts of ethylenediamine, and mixtures thereof.

5. The gel of claim 1 wherein the nonionic surfactant is a propylene glycol initiated polyoxypropylene-polyoxyethylene nonionic surfactant having an average polyoxypropylene hydrophobe of about 4,000 and a polyoxyethylene hydrophile content of about 70 percent by weight of the surfactant.

6. The gel of claim 1 wherein the nonionic surfactant is a propylene glycol initiated polyoxypropylene-polyoxyethylene nonionic surfactant having an average polyoxypropylene hydrophobe of about 3,250 and a polyoxyethylene hydrophile content of about 70 percent by weight of the surfactant.

7. The gel of claim 1 wherein the nonionic surfactant is an N,N,N',N'-tetrakis(2-hydroxylpropyl)ethylenediamine initiated polyoxypropylene-polyoxyethylene nonionic surfactant having an average polyoxypropylene hydrophobe of 6,500 to 7,000 and a polyoxyethylene hydrophile content of about 80 percent by weight of the surfactant.

8. The gel of claim 1 wherein the nonionic surfactant is a 1,4-butanediol initiated polyoxybutylene-polyoxyethylene nonionic surfactant having an average polyoxybutylene hydrophobe of about 3,000 and a polyoxyethylene hydrophile content of about 80 percent by weight of the surfactant.

* * * * *